United States Patent
Mondloch et al.

(10) Patent No.: US 7,629,570 B2
(45) Date of Patent: Dec. 8, 2009

(54) LED LIGHTING SYSTEM FOR USE IN ENVIRONMENTS WITH HIGH MAGNETICS FIELDS OR THAT REQUIRE LOW EMI EMISSIONS

(75) Inventors: Michael J. Mondloch, Waukesha, WI (US); Harry M. Pyne, New Berlin, WI (US); David Venhaus, West Allis, WI (US)

(73) Assignee: Everbrite, LLC, Greenfield, WI (US)

( * ) Notice: Subject to any disclaimer, the term of this patent is extended or adjusted under 35 U.S.C. 154(b) by 0 days.

(21) Appl. No.: 11/604,118

(22) Filed: Nov. 24, 2006

(65) Prior Publication Data

US 2007/0121328 A1    May 31, 2007

Related U.S. Application Data

(60) Provisional application No. 60/739,638, filed on Nov. 26, 2005.

(51) Int. Cl.
*G01J 1/04* (2006.01)
(52) U.S. Cl. .................................. 250/227.11; 362/249
(58) Field of Classification Search ................. 362/240, 362/373; 315/85, 291, 169.1; 600/410
See application file for complete search history.

(56) References Cited

U.S. PATENT DOCUMENTS

| 6,354,714 | B1 | 3/2002 | Rhodes |
| 6,367,949 | B1 * | 4/2002 | Pederson .................... 362/240 |
| 6,371,637 | B1 | 4/2002 | Atchinson et al. |
| 6,600,274 | B1 | 7/2003 | Hughes |
| 6,609,804 | B2 | 8/2003 | Nolan et al. |
| 6,786,625 | B2 | 9/2004 | Wesson |
| 6,860,628 | B2 | 3/2005 | Robertson et al. |
| 6,871,981 | B2 | 3/2005 | Alexanderson et al. |
| 6,880,952 | B2 | 4/2005 | Kiraly et al. |
| 7,511,259 | B2 * | 3/2009 | Nyffenegger et al. .. 250/227.11 |

\* cited by examiner

*Primary Examiner*—Anabel M Ton
(74) *Attorney, Agent, or Firm*—Michael Best & Friedrich LLP

(57) ABSTRACT

This invention is a non-ferrous lighting fixture and non-ferrous lighting system that can be used in areas with high magnetic fields or that require low EMI emissions, such as MRI operating rooms. This invention uses LED's to provide a high-intensity, quality white or other color light that is softened by reflectors and diffusers, and can be dimmed to provide flexible lighting levels. The flexible lighting levels can range from the maximum light used for patient procedures and equipment servicing/maintenance to the lowest light level used to keep a patient comfortable while facing upward on the MRI scanning table. Moreover, by using an aluminum substrate printed circuit board, this invention resolves the thermal issues associated with high-intensity lighting. Not only does this invention resolve glare and hot spot issues, it protects the user and installer from electrical hazards associated with potentially high voltages, as well. Finally, because this invention is completely non-ferrous, it does not interfere with the integrity of the MRI equipment's readings.

19 Claims, 6 Drawing Sheets

LED LIGHTING SYSTEM FOR USE IN ENVIRONMENTS WITH HIGH MAGNETICS FIELDS OR THAT REQUIRE LOW EMI EMISSIONS

CROSS REFERENCE TO RELATED APPLICATION

These inventors claim priority from U.S. Provisional patent application No. 60/739,638 filed Nov. 26, 2005.

FIELD OF THE INVENTION

This invention relates to lighting systems, specifically it is a light emitting diode (LED) lighting system that is designed entirely of non-ferrous materials and employs low RF noise driver electronics for use with high magnetic field/low electromagnetic interference (EMI) environments, such as magnetic resonance imagery (MRI) equipment applications.

DISCUSSION OF RELATIVE ART

MRI technology utilizes extremely strong magnetic fields in the order of 0.5 to over 7 Tesla. In addition, the nature of MRI signal acquisition requires a very low radio frequency (RF) noise environment to preserve image quality. These strong magnetic fields and low noise requirements pose substantial difficulties for equipment operating in the vicinity of a MRI scanner. In the past, when lighting an area that surrounds MRI equipment, facility designers had several options, including fluorescent lighting, incandescent lighting, and metal halide lighting, all of which contained ferrous metals, or materials made from iron. These designers soon discovered two(2) issues associated with the use of ferrous materials to light an area that surrounds MRI equipment.

First, ferrous materials present in the room distorted the magnetic fields that MRI equipment depended upon for reliable imaging. In extreme cases, the MRI magnet, a key component in the imaging equipment, exerted force on the current-carrying filaments in light bulbs, thereby substantially shortening the light bulbs' lives. Optimally, no ferrous materials should be placed within the 5 Gauss region of operating MRI equipment.

Second, electromagnetic radiation generated by the electron flow through discharge lighting devices (fluorescent lamps, for example) can cause MRI image failures, poor quality MRI readings, and even false MRI readings. Hence, to ensure accurate readings, some lighting systems needed to be completely shut down prior to operating the MRI equipment.

This invention is a lighting system that resolves all of the aforementioned issues. This invention produces a quality white or other color light through the use of high-intensity LED's, which can be used during MRI operation. Essentially, this invention is a direct replacement for existing incandescent and fluorescent lighting systems.

There are problems that arise from the use of high-intensity LED lighting. One problem is that LED performance and life is adversely affected by heat. This heat must be removed from the LED's themselves and effectively conducted to an area where it can be safely dissipated. This problem is further exacerbated by use of standard fiberglass circuit board (such as the circuit board used in U.S. Pat. No. 6,354,714 to Rhodes 2002, which claims a lighting strip for marking walkways and the like), which cannot be efficiently thermally-connected to a heat sink. The result is the plastic LED components can overheat and fail.

Another problem is the hot spots that are created by the intense light of the multiple LED point sources. If not corrected, these hot spots produce excessive glare and an appearance that is not aesthetically pleasing to the user.

BACKGROUND OF THE INVENTION

This invention provides a quality white or other color light that can be used during operation of MRI equipment. This quality white or other color light can be dimmed to provide flexible lighting levels. The flexible lighting levels can range from the maximum light used for patient procedures and equipment servicing/maintenance to the lowest light level used to keep a patient comfortable while facing upward on the MRI scanning table.

Moreover, by using a thermally-conductive substrate printed circuit board, this invention resolves the thermal issues associated with the high-intensity light generated by multiple LED's. The thermally-conductive printed circuit board consists of an aluminum plate that is selectively coated with an electrical insulator (coating remains only where the electrical circuits will be formed) and then forming the electrical circuits using what is known as "fully additive" circuit processes. Thus, the aluminum substrate printed circuit board creates an isolation layer and, then, a conductive layer. These layers isolate the LED's electrically, but not thermally, from the heat sink. The aluminum plate provides a direct thermal connection to the high-intensity LED components.

The lighting level issues are resolved by the incorporation of a reflector around each LED and a diffuser lens located at the light fixture's opening. This combination makes the light softer, as well as more uniform and even. This combination also protects the user and installer from electrical hazards associated with the potentially high voltages within the light fixture itself.

To date, no one has created such an MRI-compatible lighting system, and no other manufacture offers an LED lighting system for use in conjunction with operating MRI equipment.

BRIEF SUMMARY OF THE INVENTION

This invention is a lighting system consisting of a group of LED lighting fixtures wired to an alternating current (AC) mains power source and optionally interconnected to a proprietary dimmer control circuit.

The LED lighting fixtures consist of five (5) major elements: an LED light source, a beam-forming optical system, a power converter/regulator, a thermal management system, and an enclosure or supporting frame.

The LED light source consists of a thermally-conductive substrate printed circuit board with a plurality of high-intensity LED's attached. The plurality of LED's are connected electrically in series and then are connected to a constant-current source. By doing this, there is no need for "current limiting" or "series" resistors (as are needed in U.S. Pat. No. 6,871,981 to Alexanderson, et al. (2005), which claims an LED lighting system for car interiors). Current limiting series resistors create additional heat, waste electrical energy and occupy valuable space in the area of the LED's.

The beam-forming optical system consists of one or more reflectors and a translucent diffuser or lens. One or more reflectors can be employed either in conjunction with individual LED's, or to enclose a group of LED's. An array of reflectors is molded of a plastic material, such as, polycarbonate, into a single unit and metalized to provide a highly specular reflective surface. Coatings can be applied to the reflector surfaces to provide diffuse light scattering. The polycarbonate material also provides an electrical barrier to the LED circuitry, which may be operating at high voltage. The diffuser mixes the light rays from the individual LED's into a single beam of the desired radiation pattern. The diffuser also mixes any color discrepancies in the individual LED's into a uniform, homogeneous colored beam. The diffuser additionally removes the glare of the individual LED point light sources. Lastly, the diffuser lens provides an additional protection barrier for the user and the installer from the electrical hazards associated with the potentially high voltages within the light fixture itself.

The diffuser can be made of glass, plastic or any material which efficiently transmits light. It can be molded into a refracting lens or series of lenses. It can also be made of a clear substrate material with optical treatments applied to it. One such treatment involves the use of non-imaging microstructure materials that incorporate a multitude of miniature "lenses" engineered to provide a controlled radiation pattern with a high degree of light transmission. The use of a multitude of micro-lenses causes the desired mixing of the individual LED light rays without creating visible images of the point sources or color variations.

A large, single reflector encloses the LED source, reflector array, and diffuser to create a unified "light engine." Generally, this light engine is installed in a ceiling opening and appears to an observer as an ordinary incandescent light fixture.

The power converter/regulator converts mains power (typically 120 to 240 Volts AC) to a regulated DC current that can operate the LED's at a given light level. This AC to DC converter uses switching technology to reduce the heat dissipation and maximize the current source's power efficiency. Switching converters generally have a fundamental frequency associated with their design. For this invention, it is best to select a frequency and wave shape that does not cause MRI-sensitive radio frequency emissions. Additional circuit components are selected to virtually eliminate electromagnetic radiation that would interfere with operating MRI equipment. The circuit topology is designed for easy addition of Power Factor Correction (PFC) for use where required by government regulations.

The thermal management system removes heat from the LED devices and dissipates that heat into the environment. It consists of the aluminum substrate printed circuit board to which the LED's are mounted and a heat sink assembly. The thermally-conductive substrate printed circuit board creates an electrical circuit for interconnecting the LED's and conducts heat away from them much more effectively than a traditional fiberglass substrate printed circuit board. The thermally-conductive substrate printed circuit board is thermally bonded to the heat sink, which is extruded thermally-conductive with sufficient heat radiating and emission area as well as sufficient thermal conductivity to the heat radiating surfaces.

The enclosure or supporting frame mechanically connects the various optical, thermal, and electronic subassemblies and provides a means for mounting the integrated fixture into a ceiling or wall structure. The most common version of the enclosure or supporting frame is called a "down light," but other configurations are possible (wall sconces, indirect lighting, etc.). The down light fixture is typically mounted in a recessed ceiling tile or drywall ceiling. In order to facilitate installation, the down light fixture is designed to be supplied in two(2) major parts: (1) the "basic frame," which includes the supporting elements, power converter/regulator, and electrical junction box; and (2) the "light engine," which consists of the LED array, optical assembly, and thermal management components. The basic frame is installed above the ceiling, and the light engine is inserted from below the ceiling and captured by spring clips in the frame. The basic frame and light engine are then electrically connected by a connector harness.

The end result is that the radiation issues associated with florescent, incandescent, or metal halide lighting systems have been eliminated, without the thermal, glare, and hot spot issues associated with high-intensity LED lighting. This combination of elements has never been used to create such a lighting system, and no other manufacturer offers a product such as this.

DRAWINGS

Reference Numerals

200—Basic frame
201—Beam shaping lens
202—Main reflector
203—Support legs (for the diffuser)
204—Reflector array
205—(High-power) LED's
206—Heat sink
207—Aluminum substrate printed circuit board
208—Power converter/regulator assembly
209—Electrical field wiring junction box

DETAILED DESCRIPTION OF THE PREFERRED EMBODIMENT

Lighting System

Figure 1:
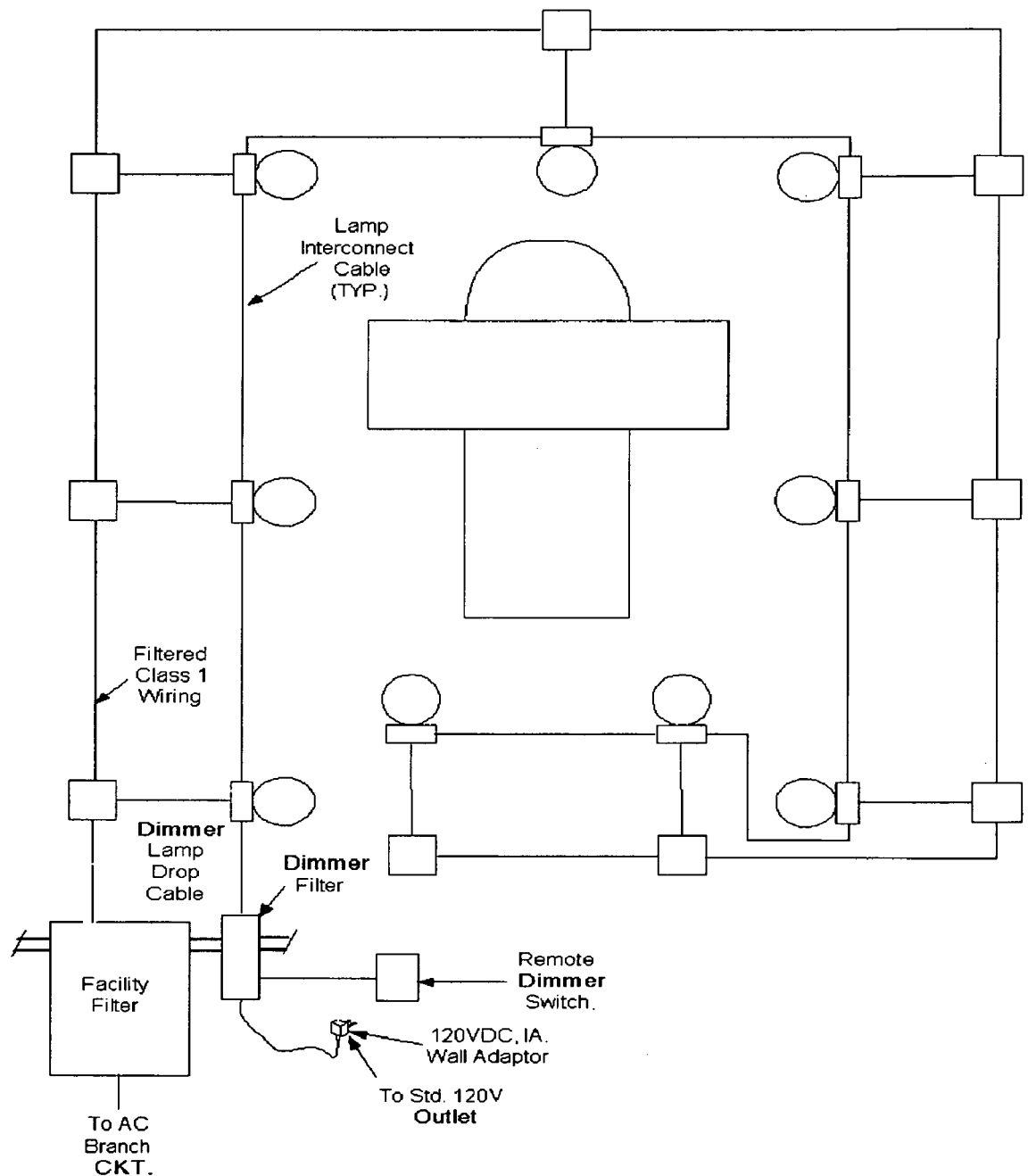
FIG. 1—Block diagram of a typical MRI room
FIG. 2—LED lighting fixture and its components
FIG. 3A—Assembly Diagram of the LED Light Source Panel
FIG. 3B—Side view of Assembly Diagram of the LED Light Source Panel
FIG. 4—Reflector Array
FIG. 5A—Schematic diagram of the LED PC Board
FIG. 5B—Schematic diagram of the Current Source Driver

FIG. 1 is a block diagram of a typical MRI room. The MRI magnet imaging equipment and patient table are centrally located in the room, which is (and must be) enclosed by an electromagnetic shield. This shield must include all doors, windows, vents, and any other penetrations into the room.

The LED lighting fixtures LF1 through LF9 are powered by ordinary mains AC supplied via junction boxes and conduit as specified by applicable electrical codes. Power for the lighting circuit is supplied to the room through an EMI facility filter installed on the outside of the room shield on a penetration panel. This ensures that any EMI signals on the power line are removed or reduced to an acceptable level before entering the room.

The LED lighting fixtures are optionally connected to a dimmer control circuit via low-voltage Class 2 Lamp Interconnect Cables in a "daisy-chain" fashion. The dimmer control circuit also passes through a filter on the penetration panel to remove any EMI from outside the MRI room. The actual dimmer control and power supply are typically located remotely outside the room.

LED Lighting Fixture

Figure 2:
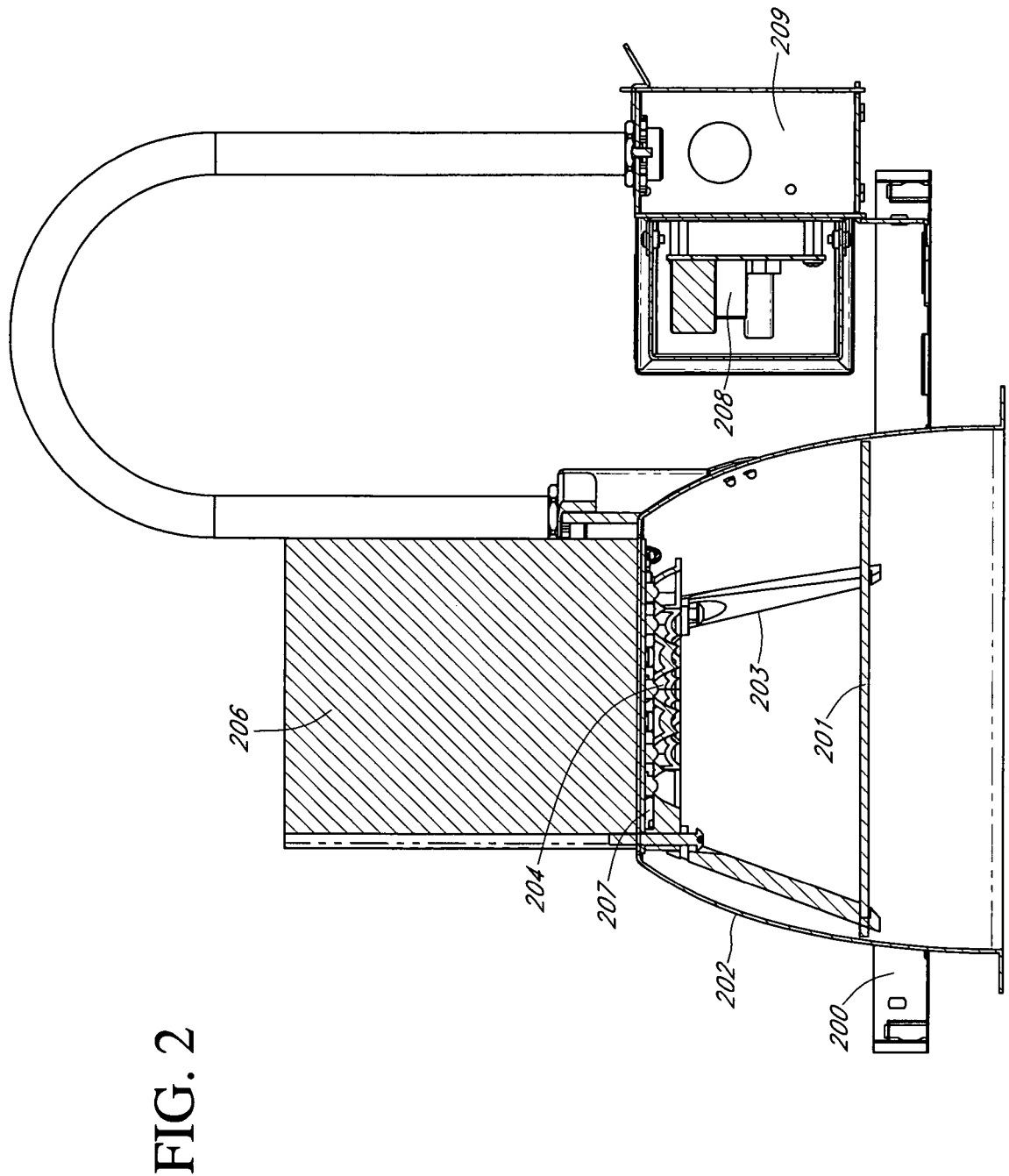

FIG. 2 depicts the LED lighting fixture and its components. The basic frame 200 supports the various components, including the power converter/regulator assembly 208, the electrical field wiring junction box 209 and spring clips, which engage the light engine. The light engine consists of the LED array, optical assembly, and thermal management components. The basic frame is installed above the ceiling, and the light engine is inserted from below the ceiling and captured by spring clips in the frame. The basic frame and the light engine are then electrically connected by a shielded wire harness. All of the fixture components are manufactured from non-ferrous materials, such as aluminum, stainless steel, brass, copper, and various types of plastic or glass.

LED Light Source & Thermal Management

Figure 3A:
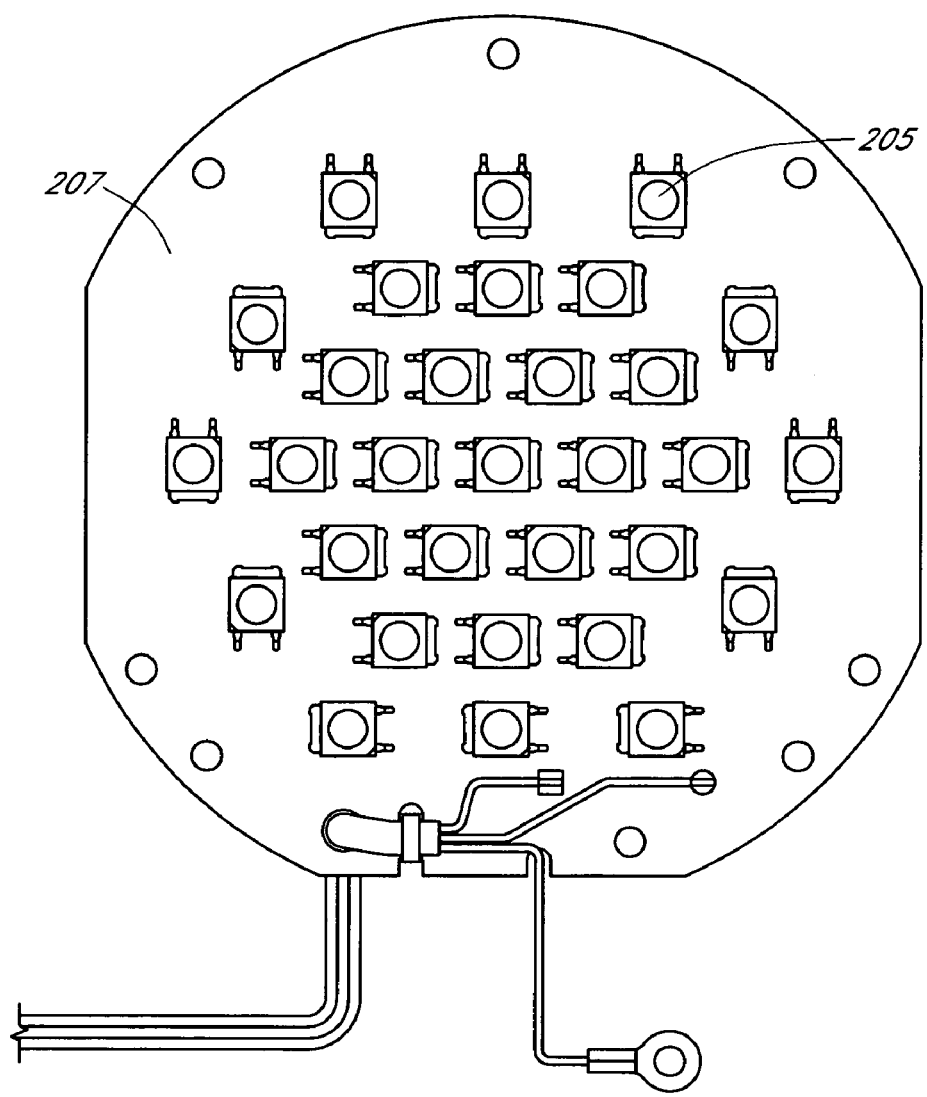
Figure 3B:
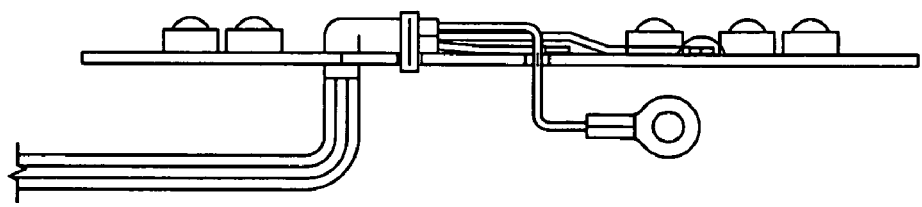

The LED light source is comprised of an aluminum substrate printed circuit board 207 (PCB) with LED's, and the primary heat sink 206. FIG. 3 shows the aluminum PCB containing thirty-one (31) high-power LED's 205 mounted in a symmetrical or nearly symmetrical array. The base material is aluminum with a dielectric coating applied to the surface. On top of this surface are conductive traces that provide a means of creating an electronic circuit board. This combination allows heat from the LED's to conduct through to the main heat sink. The LED's are electrically connected in a series arrangement so that the drive current from the power converter/regulator passes through each LED, and each LED "sees" the same electrical current. Optionally, the LED circuit may contain a thermal cutout device, protecting the LED's and fixture from overheating.

Optics

Figure 4:
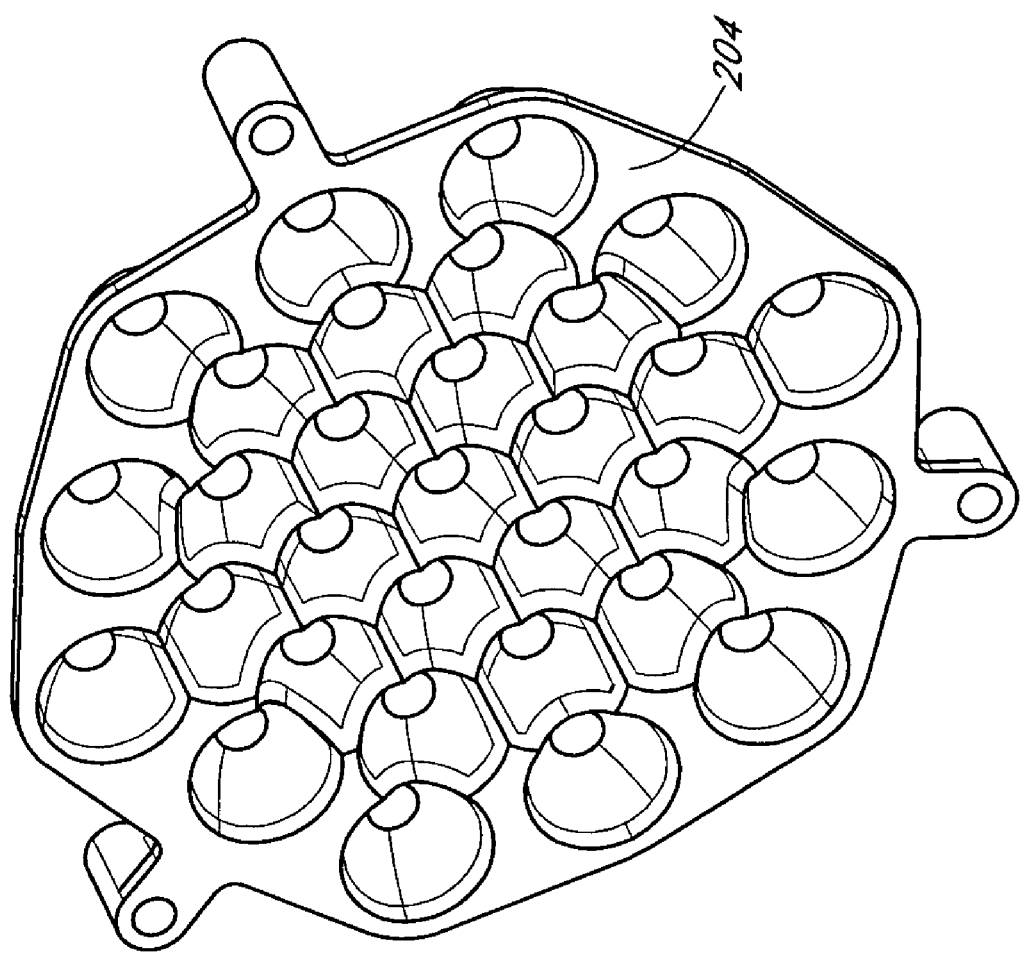

The cross section of FIG. 2 shows the three(3) major optics components: a reflector array 204 or series of individual reflectors, a beam-shaping lens 201 or diffuser, and a main reflector 202. The reflector array is comprised of either a series of parabolas, or individual parabolas, each with its focal point located at the point of radiation of its respective LED's 205. The parabolas have a specular (or diffuse) reflective coating so as to collimate the light emitted by their respective LED's. Additionally, the base material of the reflectors is such that it provides a dielectric barrier between the outside world and the aluminum PCB. FIG. 4 illustrates the reflector array.

The beam-shaping lens is comprised of a plate of optical grade material with a series of optical elements designed to provide a specific spread or beam pattern. It may be glass, plastic, or other suitable optical grade material. The optical elements may vary micro-structures to 4-5 mm across. The distance from the beam-shaping lens to the LED's is set by a mounting structure so as to maintain a constant distance from the LED's.

The main reflector is an aluminum parabola with a specular (or diffuse) finish and the aluminum substrate PCB mounted at or near its focal point. This reflector serves to gather light not managed by the reflector array and redirect it in the desired direction (towards the beam-shaping lens). This reflector serves as a mounting structure for the aluminum substrate PCB/heat sink assembly, acts as a secondary heat sink for the system, and provides an electrical enclosure for the LED circuitry.

Various combinations of these components can be used, depending on the desired illumination characteristics and system cost. The minimal configuration would consist of the LED array and overall reflector only. In order to reduce glare and spread the illumination pattern, the diffuser is added. For a more focused beam, the reflector array is employed, with or without the diffuser.

In the preferred embodiment, the LED array is matched to a metalized reflector array to effectively collimate the beam into a diffuser constructed of micro-lenses. The main overall reflector encloses the entire optics assembly and provides the mechanical structure that engages the frame's spring clips and to which the LED and heat sink assemblies are attached.

Power Converter/Regulator

Figure 5A:
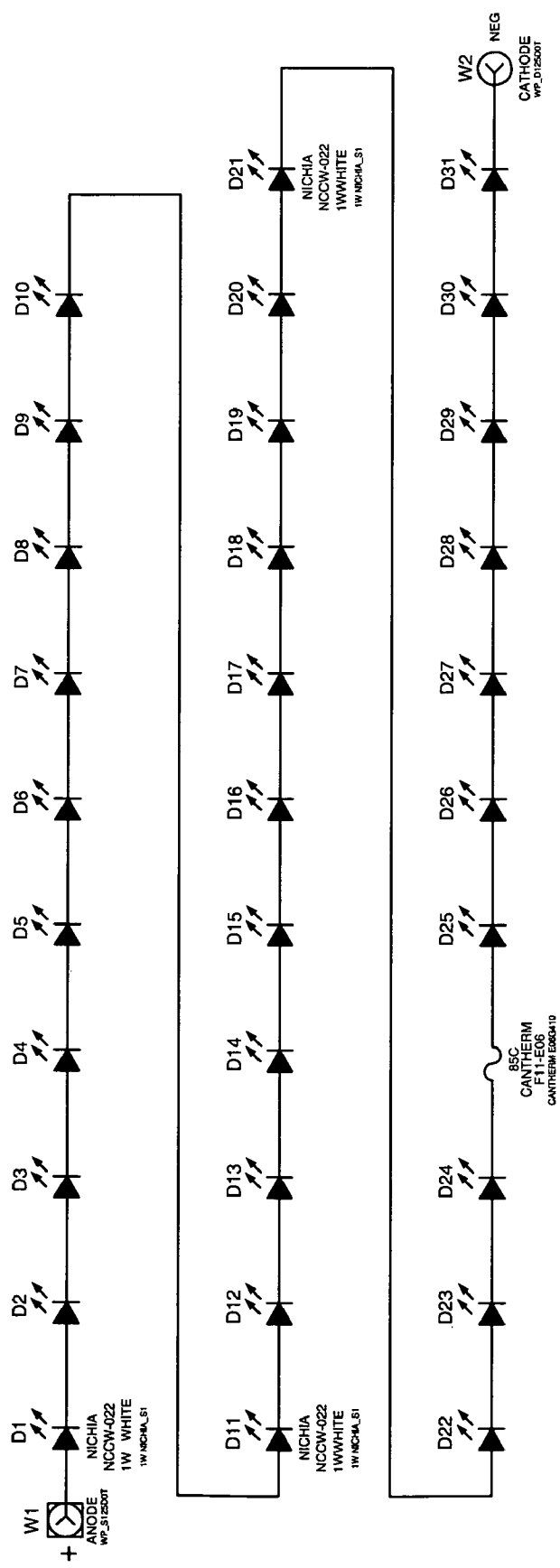
Figure 5B:
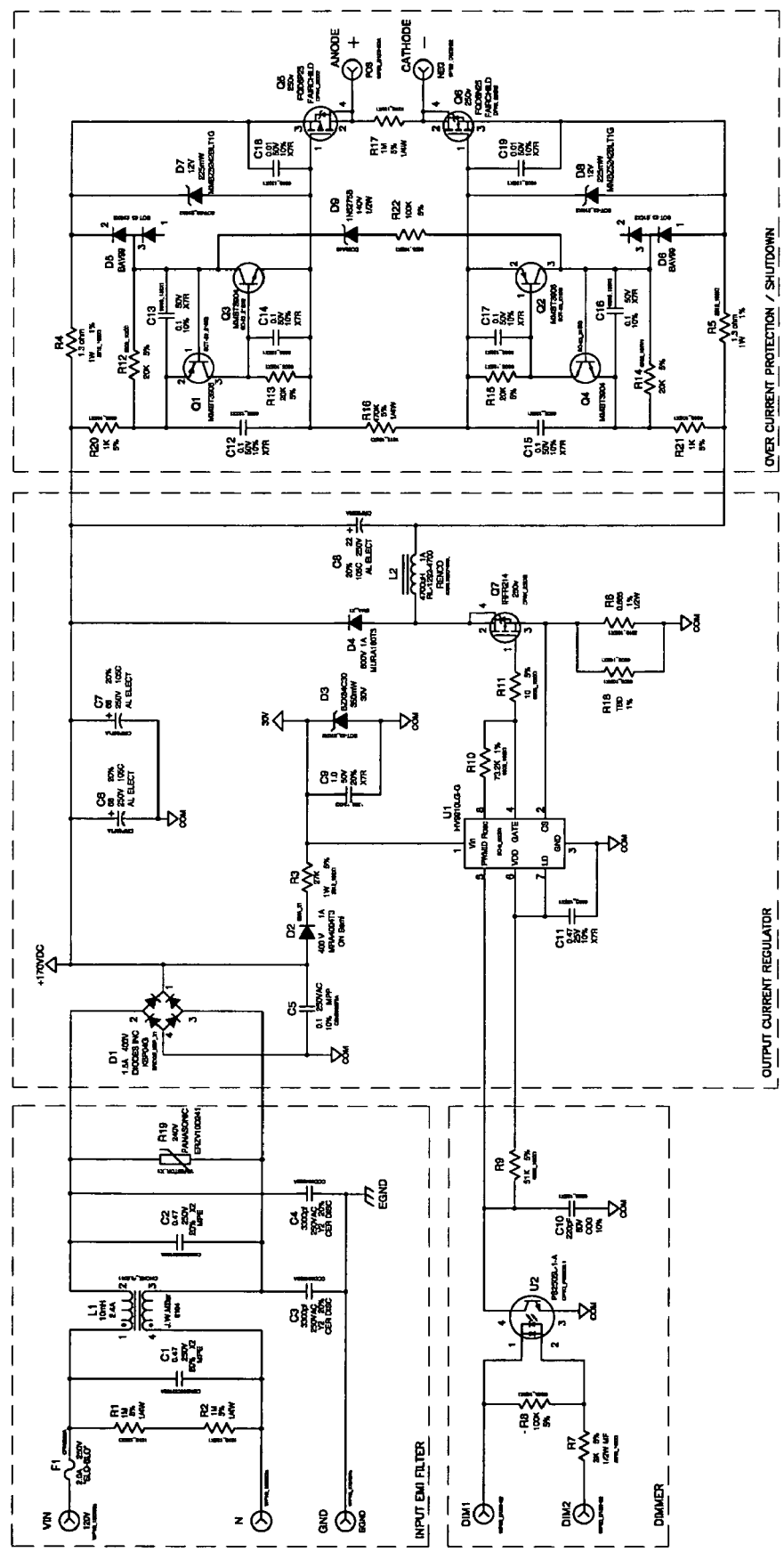

The power converter/regulator is comprised of four(4) major functional sections: Input EMI Filter; Output Current Regulator; Dimming Control; and Over Current Protection/Shutdown. These are shown on FIG. 5.

The Input EMI Filter section, comprised of suppression capacitors C1, C2, C3, and C4, and Common Mode choke L1, provides sufficient attenuation of radio frequency signals detrimental to the MRI environment that may be conducted out through the mains power wiring. Additional components, known as feed-through capacitors, provide the required attenuation of radiated radio frequency signals. Resistors R1 and R2, and varistor R19 provide the safety functions of input capacitive discharge and mains surge protection respectively.

The Output Current Regulator section serves two(2) major functions: to convert the mains AC current into a DC current, and to control the DC output voltage so that a constant current is applied to the load. Bridge rectifier D1 and bulk capacitors C6 and C7 convert the mains AC to a relatively constant voltage of approximately $Vin(RMS) \times \sqrt{2}$. For a typical 120V utility, this voltage is approximately 170V. Capacitor C5 provides a very low impedance current reservoir for high-frequency switching purposes. Diodes D2 and D3, R3 and C9 tap off this 170V bus to provide a low-current bias supply for the control circuitry at about 30V. Connections for additional Power Factor Correction circuitry are easily provided by removing jumpers and installing an optional module.

To understand the operation of the current regulation circuitry, it is helpful to imagine a load impedance in parallel with output capacitor C8, and to ignore the protection circuitry that exists beyond that point. The integrated circuit control chip, U1, provides output current regulation by switching a power transistor, Q7, OFF for a fixed period of time and then ON for variable period in response to a feedback signal generated across sense resistors R6 and R18. When the transistor is turned ON, current flows from the 170V bus, through the load, through inductor L2, through Q7, and finally through R6 and R18. The inductor limits the current's rate of increase linearly until the level reaches the control chip's internal set point determined by the value chosen for R6 and R18. At this point, the transistor is commanded to turn OFF. In response to this, L2 attempts to maintain the existing current flow by reversing polarity, forward biasing diode D4, and continuing to power the load. The fixed OFF time is chosen to allow the inductor current to drop to a set constant value before the next ON cycle begins. The resulting wave-shape is a triangle with average DC levels that equal the desired load current. Any change in input voltage or output load is compensated for by a proportional change in the ON time caused by the feedback signal across the sense resistors. This triangular wave-shape is important to the use of this circuit in low EMI environments, such as rooms with operating MRI equipment. The triangular wave-shape does not contain the multitude of harmonic frequencies that make up the square wave-shapes typically employed in switch mode regulators.

Dimming Control is provided by optical coupler U2, resistors R7, R8, and R9, and capacitor C10. Because the dimming system uses Class 2 wiring for ease of installation, it must be galvanically isolated from the current regulator circuitry, which itself operates at mains potential. The optical coupler performs the isolation function and eliminates potential wiring errors by allowing non-polarized signal connections. Resistors R7 and R8 create a voltage divider that adds some level of noise immunity and guarantees that the opto-coupler will be OFF if no signal is applied. The output side of the opto-coupler enables or disables the current control chip, thereby creating a "pulse group modulation" whereby either full current, or no current is applied to the load at a rate that is fast enough to be undetectable to the naked eye. Modulation applied in this fashion results in very linear apparent dimming without affecting the color temperature of the LED's. Resistor R9 and capacitor C10 provide additional noise filtering and a "pull-up" function that keeps the control chip active if the opto-coupler is deactivated.

Finally, the Over Current Protection/Shutdown provides a measure of safety in the event of a component failure or external wiring short circuit. There are actually two(2) distinct and separate circuits involved that are mirror images of each other. One monitors the positive load output terminal, while the other monitors the negative terminal. Field Effect Transistor (FET) Q5 (Q6) and sense resistor R4 (R5) are connected in series with the current regulator output node and the load. The transistor is sized to handle 2× the continuous load current and is initially held in the ON state by current flow through R16 and D8 (D7). At normal output current levels, the voltage drop across the sense resistor is insufficient to forward-bias sense transistor Q1 (Q4). However, when the output current reaches a fault level, current flows through R20 (R21), Q1 (Q4), and D5 (D6). As Q1 (Q4) turns ON, current flows through Q3 (Q2) creating positive feedback which causes the circuit to latch ON. This action in turn brings the gate of Q5 (Q6) to within 1.5V of its source thereby causing Q5 (Q6) to turn OFF. The total response time is fast enough to protect a semiconductor load from excessive power dissipation, even with several amperes of peak current applied. D5 (D6) allows the latch to continue to operate once the load is removed by isolating the base of Q1 (Q4) from the output node. Resistors R12 (R14) and R20 (R21), and capacitor C13 (16) set the trip response time, which can mimic any typical fuse response from "fast" to "slow blow," while R13 (R15) and C14 (C17) provide an initial turn-on delay to avoid transient nuisance tripping. Clamp diodes D7 and D8 protect the FET gates from excess voltages. Lastly, D9 and R22 provide a current path between the two(2) shutdown circuits that causes one or both latches to activate if the output terminal voltage rises above mandated safety levels, i.e. over-voltage protection.

The power converter/regulator and dimmer circuits are enclosed in a non-ferrous Farady shield to prevent radiated emissions, which would interfere with the MRI scanner signals. To prevent conducted emissions on the power input, LED output, and dimmer control leads, feed-through capacitors FC1 through FC6 are employed at the points these conductors enter/exit the shield enclosure.

We claim:

1. A non-ferrous lighting fixture comprising:
   at least one LED light source; and
   a low-noise LED power converter comprising a constant output current regulator, one or more electromagnetic filter elements, and an electromagnetic-shielded enclosure having a non-ferrous Faraday shield, whereby the outputs of the power converter are electrically connected to said LED light source.

2. The non-ferrous lighting fixture of claim 1, wherein said LED light source comprises an array of LEDs electrically connected in series and mounted on a thermally-conductive substrate.

3. The non-ferrous lighting fixture of claim 1, wherein said low-noise power converter further comprises a dimming circuit with Class 2 input characteristics.

4. The non-ferrous lighting fixture of claim 1, wherein said low-noise power converter further comprises output lead over-current sensing and shutdown circuits.

5. The non-ferrous lighting fixture of claim 1, wherein said constant output current regulator further comprises a triangular wave shape.

6. The non-ferrous lighting fixture of claim 1, wherein said constant output current regulator further comprises a fundamental operating frequency outside the typical MRI-sensitive spectrum.

7. The non-ferrous lighting fixture of claim 1, further comprising a beam-forming optical system mechanically connected to said LED light source.

8. The non-ferrous lighting fixture of claim 7, wherein said beam-forming optical system comprises a beam-forming reflector, geometry which focuses light in a forward direction to control beam angle, injection-molded structure having sufficient insulating and flame-retardant properties to act as an electrical safety barrier, and a highly reflective coating.

9. The non-ferrous lighting fixture of claim 8, wherein said highly reflective coating is specular in nature.

10. The non-ferrous lighting fixture of claim 8, wherein said highly reflective coating is diffuse in nature.

11. The non-ferrous lighting fixture of claim 7, wherein said beam-forming optical system comprises a beam-forming reflector array.

12. The non-ferrous lighting fixture of claim 7, wherein said beam-forming optical system comprises a beam-forming lens providing a homogenous, single spot light, a controlled beam shape and divergence or convergence angles, and an electrical barrier between room occupants and exposed electrical circuits.

13. The non-ferrous lighting fixture of claim 12, wherein said beam-forming lens comprises a molded lens with refractive elements.

14. The non-ferrous lighting fixture of claim 12, wherein said beam-forming lens comprises integrally-formed microstructure refractive elements.

15. The non-ferrous lighting fixture of claim 1, further comprising a thermal management system mounted to said LED light source.

16. The non-ferrous lighting fixture of claim 15, wherein said thermal management system comprises a thermally-conductive LED mounting substrate and a thermal dissipater consisting of a thermally-conductive, emissive heat sink radiator.

17. The non-ferrous lighting fixture of claim 16, wherein said thermal management system includes aluminum.

18. A non-ferrous lighting fixture comprising:
   at least one LED light source;
   a power control circuit comprising a constant output current regulator, one or more electromagnetic filter elements, and a dimming circuit with Class 2 input characteristics, and an electromagnetic-shielded enclosure having a non-ferrous Faraday shield;
   a beam-forming optical system;
   a thermal management system; and
   a ceiling mounted mechanism with outer reflector resembling a conventional recessed fixture; that connects said LED light source, said power control circuit, said beam-forming optical system, and said thermal management system together both mechanically and to a mounting means.

19. A non-ferrous lighting system comprising at least one non-ferrous lighting fixture of claim 3, wired to AC power, and interconnected to a dimmer control signal that controls said non-ferrous lighting fixture's low-noise power converter dimming circuit to dim said LED light source to the light level desired.

* * * * *

UNITED STATES PATENT AND TRADEMARK OFFICE
CERTIFICATE OF CORRECTION

PATENT NO. : 7,629,570 B2  Page 1 of 1
APPLICATION NO. : 11/604118
DATED : December 8, 2009
INVENTOR(S) : Mondloch et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 64 days.

Signed and Sealed this

Second Day of November, 2010

David J. Kappos
*Director of the United States Patent and Trademark Office*